US00PP33117P2

(12) United States Plant Patent
van Nijnatten

(10) Patent No.: US PP33,117 P2
(45) Date of Patent: Jun. 1, 2021

(54) ***SYRINGA* PLANT NAMED 'ANNY2013-02'**

(50) Latin Name: *Syringa meyeri*
Varietal Denomination: ANNY2013-02

(71) Applicant: André van Nijnatten, Zundert (NL)

(72) Inventor: André van Nijnatten, Zundert (NL)

( * ) Notice: Subject to any disclaimer, the term of this patent is extended or adjusted under 35 U.S.C. 154(b) by 0 days.

(21) Appl. No.: 16/873,823

(22) Filed: Jul. 15, 2020

(51) Int. Cl.
*A01H 5/00* (2018.01)
*A01H 6/00* (2018.01)

(52) U.S. Cl.
USPC ..... Plt./248

(58) Field of Classification Search
USPC ..... Plt./226, 248
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Syringa* plant named 'ANNY2013-02' that is characterized by its dwarf growth habit, its flowers that are large in size with panicles that are white in color and flower buds that are tinged pink in color, its flowers that have a strong and sweet fragrance, its repeat blooming in the summer with a second blooming period in autumn and its free flowering blooming habit.

2 Drawing Sheets

Botanical classification: *Syringa meyeri.*
Variety denomination: 'ANNY2013-02'.

CROSS REFERENCE TO A RELATED APPLICATION

This application is related to U.S. Plant Patent for a plant derived from the same breeding program that is entitled *Syringa* Plant Named 'ANNY2013-18' (U.S. Plant patent application Ser. No. 16/873,827).

BACKGROUND OF THE INVENTION

The present invention relates to a new and distinct cultivar of *Syringa meyeri* origin that is botanically known as *Syringa* 'ANNY2013-02' and will be referred to hereafter by its cultivar name, 'ANNY2013-02'. 'ANNY2013-02' is a new cultivar of lilac grown for use as an ornamental landscape plant.

'ANNY2013-02' was discovered by the Inventor as a chance seedling in a trial plot in Zundert, The Netherlands in July of 2013. The exact parentage is unknown, however it is most likely that *Syringa* 'Pink Perfume' (U.S. Plant Pat. No. 24,252) is a probable parent based on its characteristics and its proximity to the new cultivar.

Asexual propagation of the new cultivar was first accomplished by rootstock grafting in June of 2015 under the direction of the Inventor in Zundert, The Netherlands. Asexual propagation by rootstock grafting has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'ANNY2013-02' as a unique cultivar of *Syringa.*

1. 'ANNY2013-02' exhibits a dwarf growth habit.

2. 'ANNY2013-02' exhibits flowers that are large in size with panicles that are white in color and flower buds that are tinged pink in color.
3. 'ANNY2013-02' exhibits flowers that have a strong and sweet fragrance.
4. 'ANNY2013-02' exhibits repeat blooming in the summer and a second blooming period in autumn.
5. 'ANNY2013-02' exhibits a freely flowering blooming habit.

The probable parent of 'ANNY2013-02', 'Pink Perfume', differs from 'ANNY2013-02' in having a larger plant size and a more upright and spreading plant habit. The new *Syringa* can be most closely compared to *Syringa* cultivars 'Palibin' (not patented), 'Anny200809' (not patented), and 'ANNY2013-18'. 'Palibin' and 'Anny200809' are both similar to 'ANNY2013-02' in having flowers that are strong in fragrance. 'Palibin' differs from 'ANNY2013-02' in having a low spreading growth habit and flowers that are pink in color. 'Anny200809' differs from 'ANNY2013-02' in having a taller growth habit and flowers that are red-purple in color. 'ANNY2013-18' is similar to 'ANNY2013-02' in having large flowers. 'ANNY2013-18' differs from 'ANNY2013-02' in having panicles that are are deep pink in color with red-purple flower buds.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosure include but may not be limited to a website listing by Concept Plants; the breeder's representative for licensing future propagation.

BRIEF DESCRIPTION OF THE DRAWINGS

The accompanying colored photographs illustrate the overall appearance and distinct characteristics of the new *Syringa*. The photographs were taken of a 2.5-year-old plant as grown outdoors in 2-liter containers at a nursery in Zundert, The Netherlands.

The photograph in FIG. 1 provides a side view of a plant of 'ANNY2013-02' in bloom.

Figure 1:
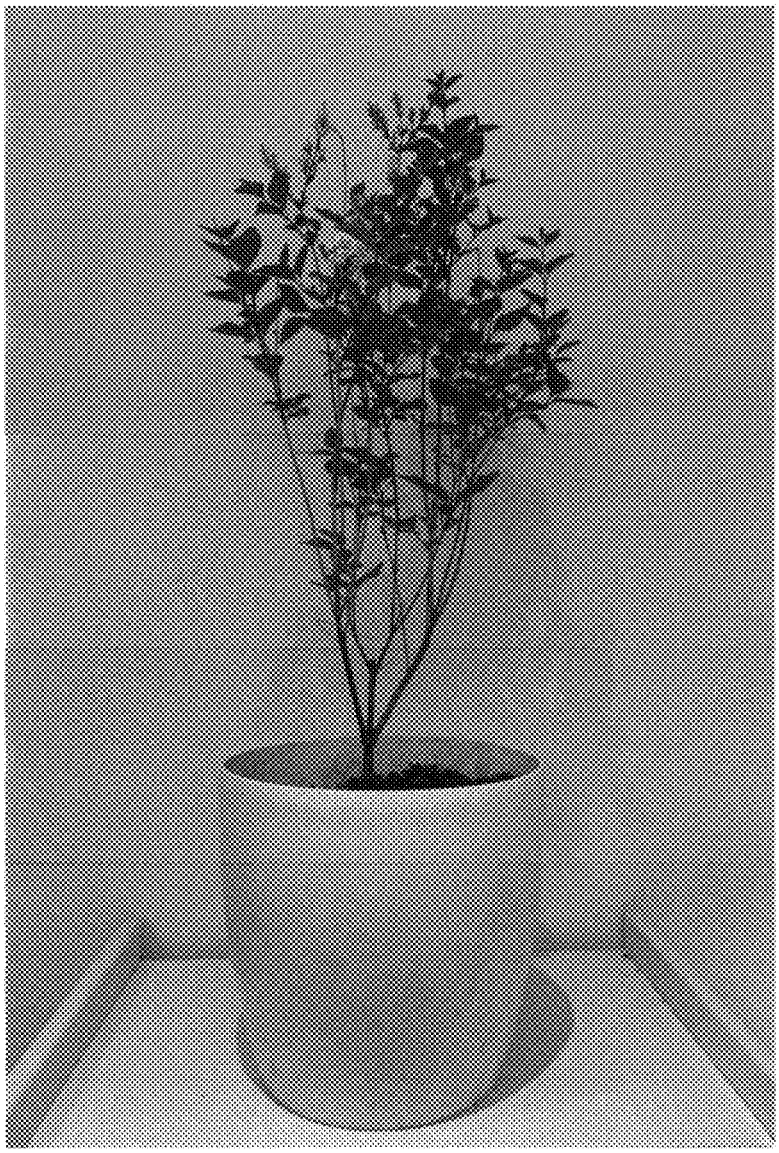
Figure 2:
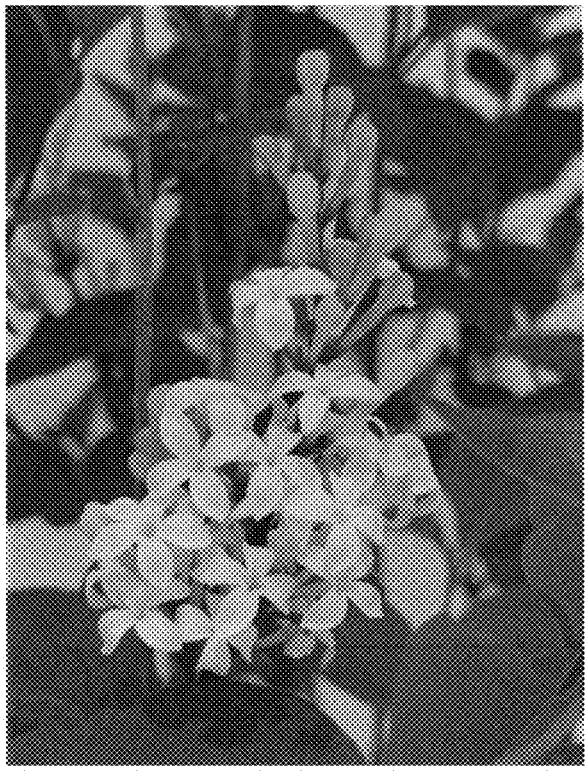

The photograph in FIG. 2 provides a close-up view of the inflorescence of 'ANNY2013-02'.

Figure 3:
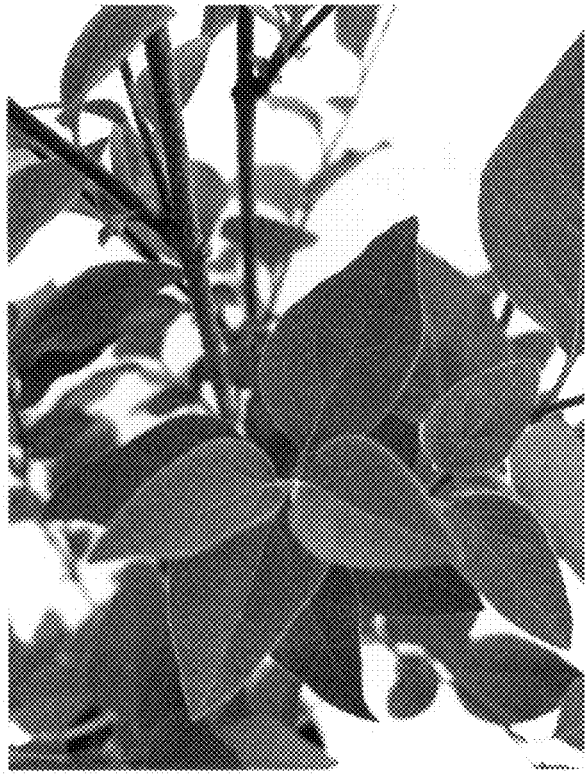

The photograph in FIG. 3 provides a close-up view of the foliage of 'ANNY2013-02'.

The colors in the photographs are as close as possible with the photographic and printing technology utilized and the color values cited in the detailed botanical description accurately describe the colors of the new *Syringa*.

DETAILED BOTANICAL DESCRIPTION

The following is a description of 2.5-year-old plants as grown outdoors in 2-liter containers in Zundert, The Netherlands. The phenotype of the new cultivar may vary with variations in environmental, climatic, and cultural conditions, as it has not been tested under all possible environmental conditions. The color determination is in accordance with the 2007 Colour Chart of The Royal Horticultural Society, London, England, except where general color terms of ordinary dictionary significance are used.

General description:

*Blooming period*.—Spring with reblooming in summer and again in Autumn in The Netherlands.

*Plant type*.—Deciduous shrub.

*Plant shape*.—Broadly upright and ovate.

*Plant habit*.—Dwarf, dense and compact.

*Height and spread*.—An average of 58 cm an height and 27 cm in width as a 2.5-year old plant in a 2-liter container.

*Hardiness*.—At least in U.S.D.A. Zones 5 through 9.

*Diseases and pests*.—No susceptibility or resistance to diseases or pests has been observed.

*Root description*.—Fibrous and dense, a blend of 165A and 161D in color.

*Propagation*.—Rootstock grafting.

*Growth rate*.—Moderate.

*Root development*.—Grafts root in 4 to 6 weeks, plugs are overwintered and planted in a P9 container following spring.

Branch description:

*Branch shape*.—Rounded.

*Branch color*.—Young stems 148A, older bark N199B.

*Branch size*.—Average of 26 cm in length, 4 mm in diameter.

*Branch surface*.—Smooth and moderately covered with soft pubescent hairs; average of 0.5 mm in length, N155A in color.

*Branch quantity*.—Average of 4 main branches, average of 5 lateral branches per main branch.

*Branch strength*.—Strong.

*Internode length*.—4 cm in length.

*Branching*.—Held upright to slightly outward.

Foliage description:

*Leaf shape*.—Ovate to broadly ovate.

*Leaf division*.—Simple.

*Leaf base*.—Obtuse.

*Leaf apex*.—Broadly acute.

*Leaf fragrance*.—None.

*Leaf venation*.—Pinnate, upper surface 145A in color, lower surface 145B in color.

*Leaf margins*.—Entire.

*Leaf arrangement*.—Opposite.

*Leaf attachment*.—Petiolate.

*Leaf surface*.—Upper and lower surface smooth and slightly leathery.

*Leaf size*.—An average of 4.2 cm in length and 3 cm in width.

*Leaf quantity*.—An average of 12 (6 pairs) per mature branch.

*Leaf color*.—Young leaves upper surface; 137C, lightly flushed with 183A at the margins, young leaves lower surface; 139C, lightly flushed with 183A at the margins, mature leaves upper surface; 137C, mature leaves lower surface; 139C.

*Petioles*.—An average of 1 cm in length and 1.5 mm in width, color; both surfaces 145A, base 177A.

Inflorescence description:

*Inflorescence type*.—Terminal and axillary panicles.

*Inflorescence size*.—An average of 9.8 cm in height and 4.6 cm in width.

*Peduncles*.—An average of 6 cm in length and 2 mm in diameter, glabrous and slightly glossy surface, moderate strength, 147B in color, held at a vertical angle.

*Flower buds*.—Spathulate in shape, average of 1 cm in length, 2 mm in diameter, color; N155B and 49D, top of bud is 38D to 38B.

*Flower fragrance*.—Sweet, strong, lilac scent.

*Persistence of flowers*.—Self-cleaning.

*Lastingness of flowers*.—Individual panicles bloom for about 10 days.

*Flower quantity*.—An average of 100 flowers per lateral stem.

*Flower type*.—Salverform.

*Flower aspect*.—Upwards and slightly outward.

*Flower size*.—An average of 7 mm in diameter, 1.3 cm in depth.

*Petals*.—4, free petal lobes; an average of 1.6 cm in length and 3 mm in width, narrow oblanceolate in shape with acute apex, entire margins, margins of the free lobes moderately involute, lower 75% fused forming a narrow tube, color; when opening upper surface 155C to 155B, tube 155C and 38D, when opening lower surface; 155C, tube 155C and 38D, when fully open upper and lower surface 155C to 155B.

*Calyx*.—Rotate, 2 mm in length, 1.5 mm in diameter.

*Sepals*.—4, base fused into a campanulate shape, rotate, margins entire, acute apex, average of 2 mm in length, 1 mm in width, color; 146C, flushed with 185B to 185C.

Reproductive organs:

*Pistils*.—1, average of 3 mm in length, stigma; club-shaped, 155A in color, style; average of 2 mm in length, 155A in color, ovary 143B in color.

*Stamens*.—4, fused into groups of 2, anthers; dorsi-fixed, sessile (no filament) and implanted into inner side of tube, an average of 3 mm in length and 182B to 182C in color, pollen; low in quantity and 158D in color.

*Fruit and seed*.—No seed or fruit has been observed to date.

It is claimed:

1. A new and distinct cultivar of *Syringa* plant named 'ANNY2013-02' as herein illustrated and described.

* * * * *